(12) United States Patent
Lauer

(10) Patent No.: US 6,277,103 B1
(45) Date of Patent: Aug. 21, 2001

(54) FLAT-SIDED LUER LOCK CONNECTORS

(76) Inventor: Mark A. Lauer, 1693 Juno Ave., St. Paul, MN (US) 55116

( * ) Notice: Subject to any disclaimer, the term of this patent is extended or adjusted under 35 U.S.C. 154(b) by 0 days.

(21) Appl. No.: 09/755,155

(22) Filed: Jan. 5, 2001

Related U.S. Application Data

(63) Continuation-in-part of application No. 09/632,123, filed on Aug. 3, 2000.

(51) Int. Cl.[7] .................................................... A61M 5/00

(52) U.S. Cl. .............................................................. 604/246

(58) Field of Search ................................... 604/246, 256, 604/523, 533, 905

(56) References Cited

U.S. PATENT DOCUMENTS

| | | | |
|---|---|---|---|
| 5,651,776 | * | 7/1997 | Appling et al. ...................... 604/283 |
| 5,928,204 | * | 7/1999 | Lopez .................................. 604/249 |
| 5,947,954 | * | 9/1999 | Bonaldo ............................... 604/533 |
| 6,050,978 | * | 4/2000 | Orr et al. ............................. 604/249 |

* cited by examiner

*Primary Examiner*—Gene Mancene
*Assistant Examiner*—Eduardo C. Robert
(74) *Attorney, Agent, or Firm*—Hugh D. Jaeger

(57) ABSTRACT

A Luer lock connector and a Luer lock injection site connector each featuring a flat surface for placing parallel to and substantially flush against the epidermis of a patient and for use generally with an intravenous catheter attached to the epidermis. Such orientation presents a wide contact surface with the epidermis which minimizes or prevents epidermal irritation.

1 Claim, 8 Drawing Sheets

FLAT-SIDED LUER LOCK CONNECTORS

CROSS REFERENCES TO CO-PENDING APPLICATIONS

This patent application is a continuation-in-part of Ser. No. 09/632,123 entitled "Suction Catheter System" filed Aug. 3, 2000, pending.

BACKGROUND OF THE INVENTION

1. Field of the Invention

The present invention relates to medical devices, and, more particularly relates to Luer lock connectors which feature a flat side.

2. Description of the Prior Art

Luer lock connectors having different constructions and functions are used with a variety of medical devices, one common medical device being an intravenous catheter. Two basic types of Luer lock connectors are commonly associated with an intravenous catheter. One type functions as a coupler which has one end configured for connection to the intravenous catheter and the other end configured for connection to a supply tube, this type being simply termed a Luer lock connector. The other type likewise has one end configured for connection to the intravenous catheter but is configured at the other end to provide an injection site, this type being more specifically termed a Luer lock injection site connector. The Luer lock connectors or Luer lock injection site connectors are taped to the skin near the site of a puncture to firmly anchor and secure the intravenous catheter within the epidermis. The tape is applied over and about the body of the Luer lock connector or Luer lock injection site connector, each of which is oriented at an angle with respect to the patient's epidermis, which causes one edge of the Luer lock connector or Luer lock injection site connector to be in intimate and forced contact with the epidermis. Such orientation and pressure often causes the one edge of the Luer lock connector or Luer lock injection site connector to dig into and to cause an indentation in the epidermis. Such an indentation can be a source of irritation and discomfort to the patient and could even be a source of localized cellulitis. Clearly what is needed is both a Luer lock connector and a Luer lock injection site connector which can be attached to the epidermis without causing trauma, stress and irritation at the region of contact with the epidermis.

SUMMARY OF THE INVENTION

The general purpose of the present invention is to provide Luer lock connectors which can be attached and secured to a patient such that no irritation or at most minimum irritation occurs at the attachment site. Such is accomplished by the instant invention which provides in one embodiment a Luer lock connector having a flat side which is oriented to align parallel to and to rest comfortably against the patient's epidermis and in an alternative embodiment a Luer lock injection site connector also incorporating a flat side.

According to one embodiment of the present invention, there is provided a flat-sided Luer lock connector including a cylindrical body truncated by a flat planar surface, a truncated disk-shaped panel extending across one end of the truncated cylindrical body, a cylindrical extension extending distally from the truncated disk-shaped panel for connection to a supply tube, and a tapered tubular member extending proximally from the interior of the truncated cylindrical body.

According to an alternative embodiment of the present invention, there is provided a flat-sided Luer lock injection site connector which includes many of the same features found in the flat-sided Luer lock connector of the first embodiment, but which is configured differently at its distal end. More specifically, rather than having a cylindrical extension at the distal end for connection to a supply tube, as does the first embodiment, the alternative embodiment has provision at its distal end for serving as an injection site.

One significant aspect and feature of the present invention is a flat-sided Luer lock connector having a flat planar surface which in use is oriented parallel to and substantially flush with a patient's epidermis.

Another significant aspect and feature of the present invention is a flat-sided Luer lock connector having a profile which minimizes or produces no epidermal irritation.

Another significant aspect and feature of the present invention is a flat-sided Luer lock connector having a surface configured for gripping while tightening.

Yet another significant aspect and feature of the present invention is a flat-sided Luer lock connector which can be readily and easily and economically produced.

A further significant aspect and feature of the present invention is a flat-sided Luer lock injection site connector, an alternative embodiment, which incorporates the above-listed significant aspects and features.

Having thus briefly described embodiments of the present invention and enumerated certain significant aspects and features thereof, it is the principal object of the present invention to provide a Luer lock connector and a Luer lock injection site connector which when utilized with an intravenous catheter and anchored to the skin at a puncture site, will rest comfortably against the epidermis and minimize, if not entirely eliminate, trauma, stress and irritation at the region of contact with the epidermis.

BRIEF DESCRIPTION OF THE DRAWINGS

Other objects of the present invention and many of the attendant advantages of the present invention will be readily appreciated as the same becomes better understood by reference to the following detailed description when considered in connection with the accompanying drawings, in which like reference numerals designate like parts throughout the figures thereof and wherein.

DETAILED DESCRIPTION OF THE PREFERRED EMBODIMENTS

Figure 1:
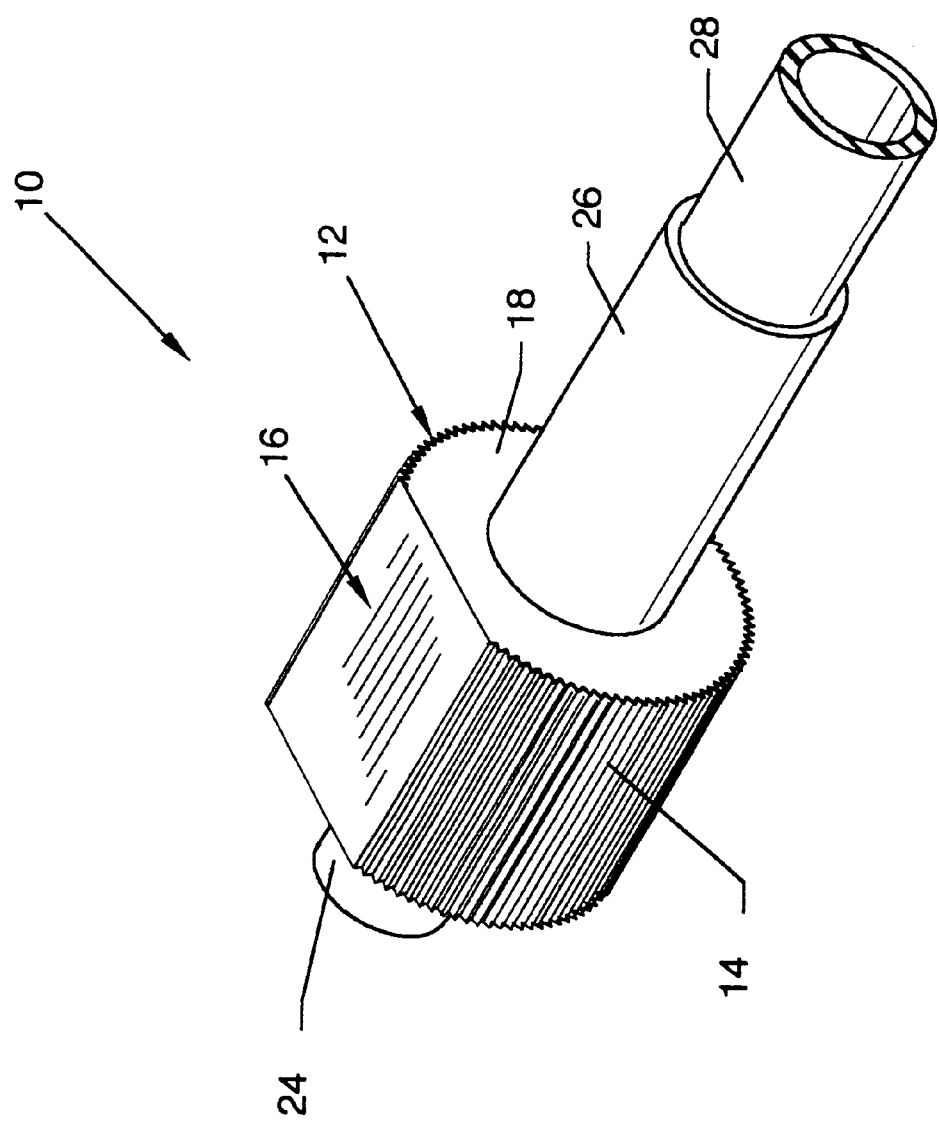
FIG. 1 illustrates an isometric view of a flat-sided Luer lock connector.
Figure 2:
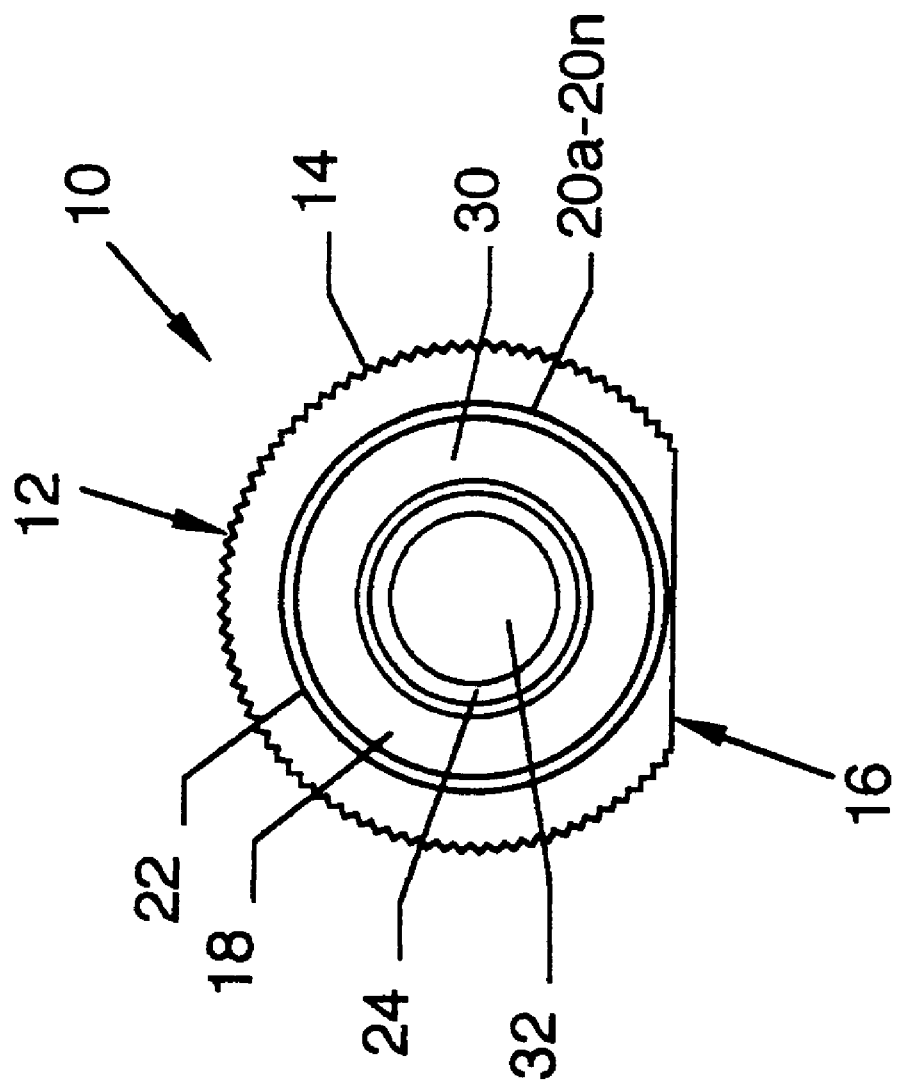
FIG. 2 illustrates a proximal end view of the flat-sided Luer lock connector.
Figure 3:
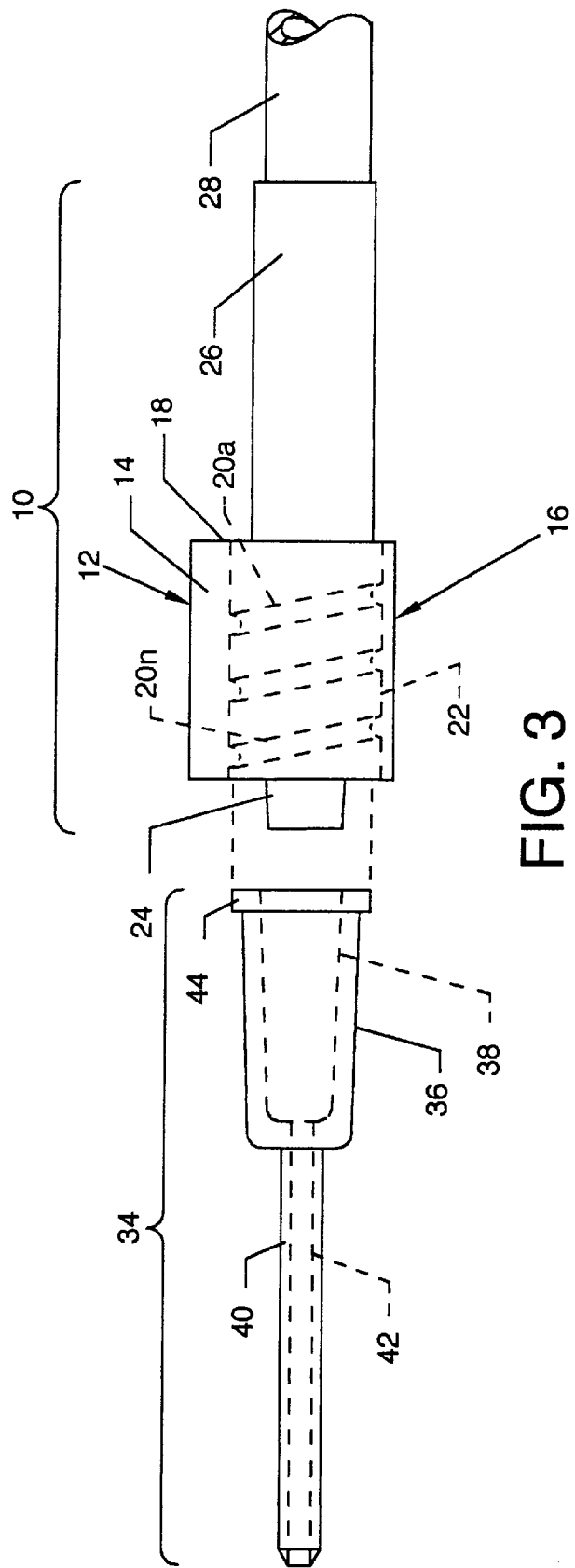
FIG. 3 illustrates a side view of the flat-sided Luer lock connector and an intravenous catheter aligned therewith prior to mutual engagement.
Figure 4:
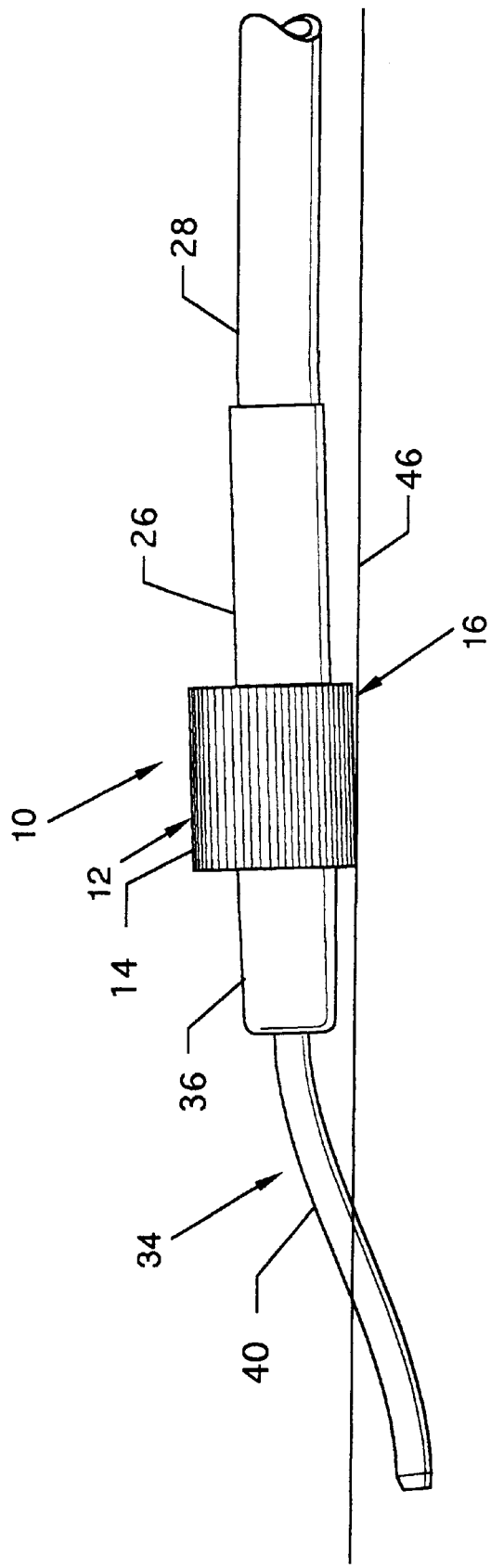
FIG. 4 illustrates the use of the flat-sided Luer lock connector with the intravenous and catheter.

FIG. 1 illustrates an isometric view of a flat-sided Luer lock connector 10. The view presented in FIG. 1 is inverted to show the features of the flat side in full. The Luer lock connector 10 features a truncated cylindrical body 12 defined by a radiused wall 14 truncated along a chord represented by a flat planar surface 16. The wall 14 intersects the circular edge of a planar disk-shaped panel 18, which is also truncated. The planar and truncated disk-shaped panel 18 extends across one end of the truncated cylindrical body 12. Wall 14 is grooved or otherwise suitably configured to allow the practitioner to effectively grip the flat-sided Luer lock connector 10. A plurality of threads 20a–20n are located on and extend inwardly from the inner curved surface 22 of the truncated cylindrical body 12, as shown in FIGS. 2 and 3, to mate with a suitable intravenous catheter 34 (FIG. 3). After engagement of the intravenous catheter 34 with the flat-sided Luer lock connector 10, the intravenous catheter 34 and the flat-sided Luer lock connector 10 are orientated with the flat planar surface 16 parallel to and substantially flush against the epidermis 46 (FIG. 4). A tapered tubular member 24 extends proximally and concentric to and along the centerline of the truncated cylindrical body 12 for subsequent frictional engagement to and with the intravenous catheter 34. Extending distally and in opposition to the tapered tubular member 24 and from the planar and truncated disk-shaped panel 18 is a cylindrical extension 26 the center of which accommodatingly serves as an attachment fixture for a supply tube 28. Tapered tubular member 24 and cylindrical extension 26 include a common passage 32 (FIG. 2) which also extends through the planar and truncated disk-shaped panel 18 for passage of medicinal fluids through the flat-sided Luer lock connector 10. An annular space 30 (FIG. 2) is included between the inner curved surface 22 and the tapered tubular member 24 for accommodation of an intravenous catheter. The truncated parts 12 and 18 impart an overall low profile to the flat-sided Luer lock connector 10. Alternatively, the truncated cylindrical body 12 and the attributes thereof can be incorporated into use with a slip Luer lock connector (not illustrated). A slip Luer lock connector is a Luer lock connector that can slide back and forth about one-third of an inch toward the end of the supply tube to engage an intravenous catheter.

FIG. 2 illustrates a proximal end view of the flat-sided Luer lock connector 10. Illustrated in particular is the common passage 32 passing through the tapered tubular member 24, the planar and truncated disk-shaped panel 18, and the cylindrical extension 26.

FIG. 3 illustrates a side view of the flat-sided Luer lock connector 10 and an intravenous catheter 34 aligned therewith prior to mutual engagement. The intravenous catheter 34 includes a tapered body 36 having a tapered interior 38, a slender cylinder 40 extending from the tapered body 36, and a passage 42 in the cylinder 40 connected to and communicating with the tapered interior 38. A flange 44 is located at one end of the tapered body 36 for engagement with the interior threads 20a–20n of the truncated cylindrical body 12.

FIG. 4 illustrates the use of the flat-sided Luer lock connector 10 with the intravenous catheter 34. In use, the slender and flexible cylinder 40 of the intravenous catheter 34 is inserted through the epidermis 46, and the flat-sided Luer lock connector 10 is anchored in place by taping it to the epidermis 46 with the flat planar surface 16 thereof oriented such that it lies substantially flush against the epidermis 46. Due to the flat planar surface 16 lying substantially flush against the epidermis 46, adverse effects such as trauma, irritation, stress and the like resulting from impingement of the epidermis 46 by the flat-sided Luer lock connector 10 are either non-existent or exceedingly minor in nature.

Figure 5:
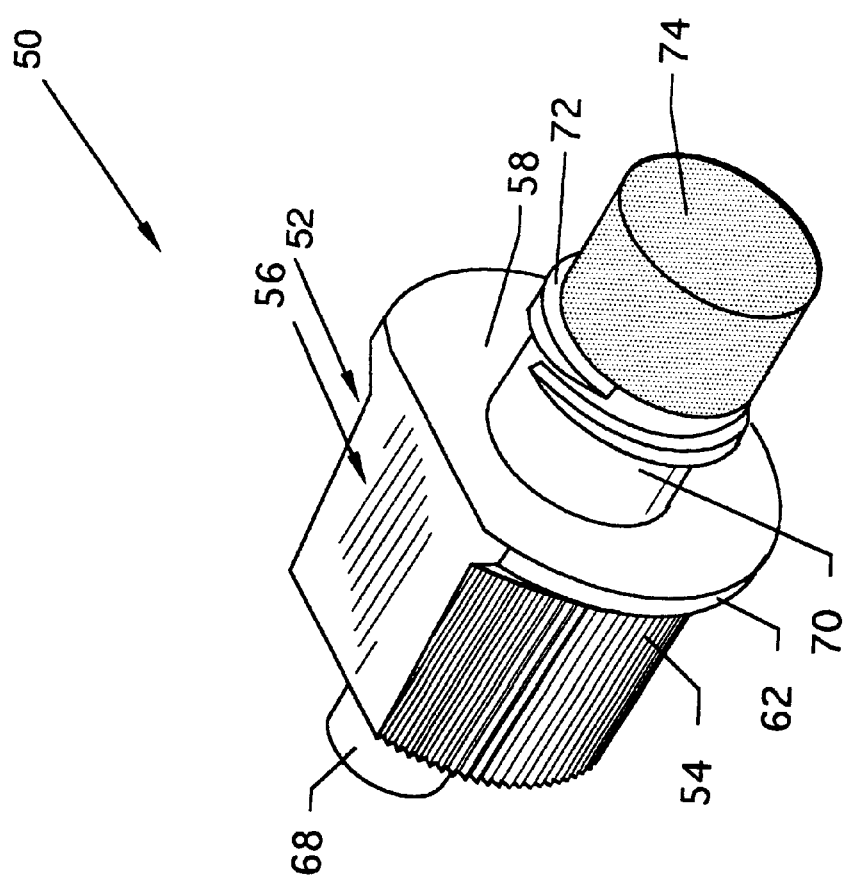
FIG. 5, an alternative embodiment, illustrates an isometric view of a flat-sided Luer lock injection site connector.
Figure 6:
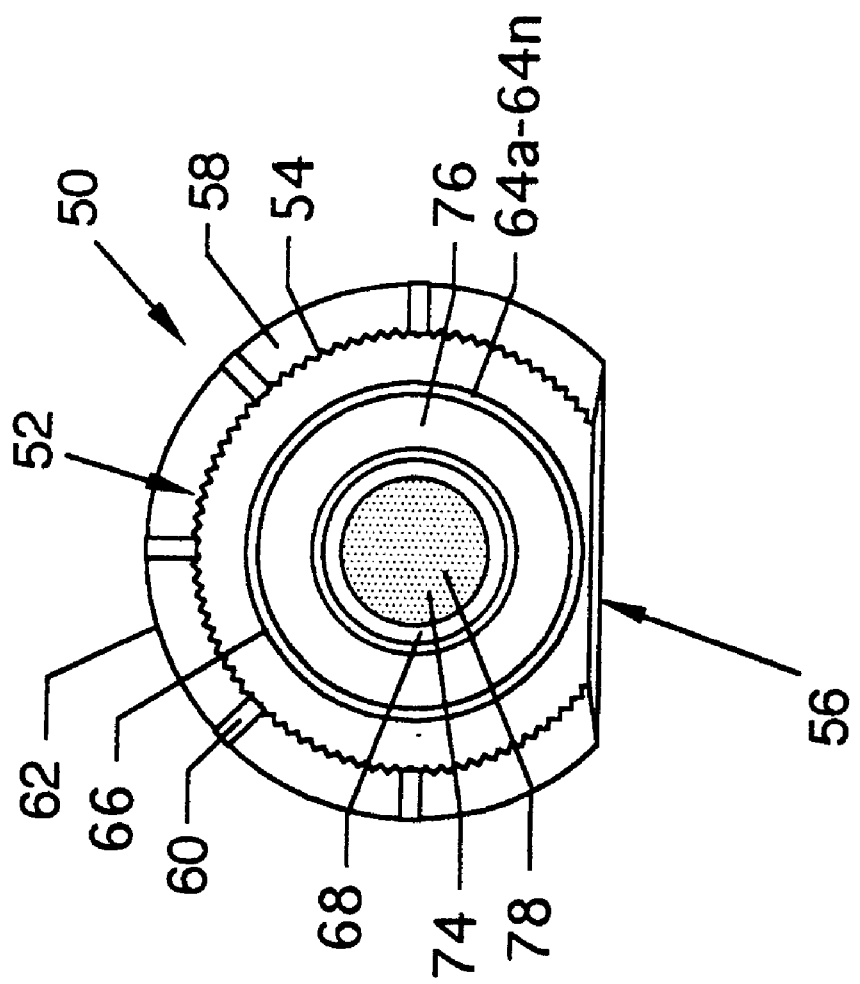
FIG. 6 illustrates a proximal end view of the flat-sided Luer lock injection site connector.
Figure 7:
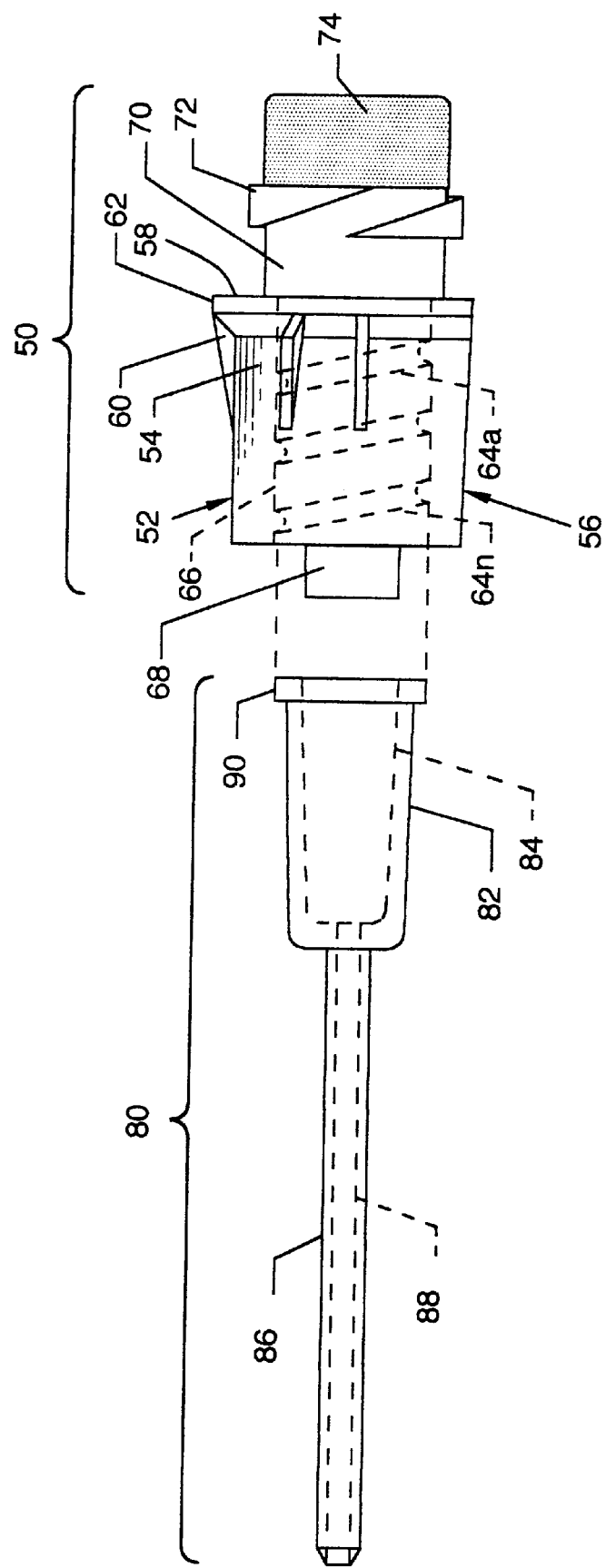
FIG. 7 illustrates a side view of the flat-sided Luer lock injection site connector and an intravenous catheter aligned therewith prior to mutual engagement; and, FIG. 8 illustrates the use of the flat-sided Luer lock injection site connector with the intravenous catheter.
Figure 8:
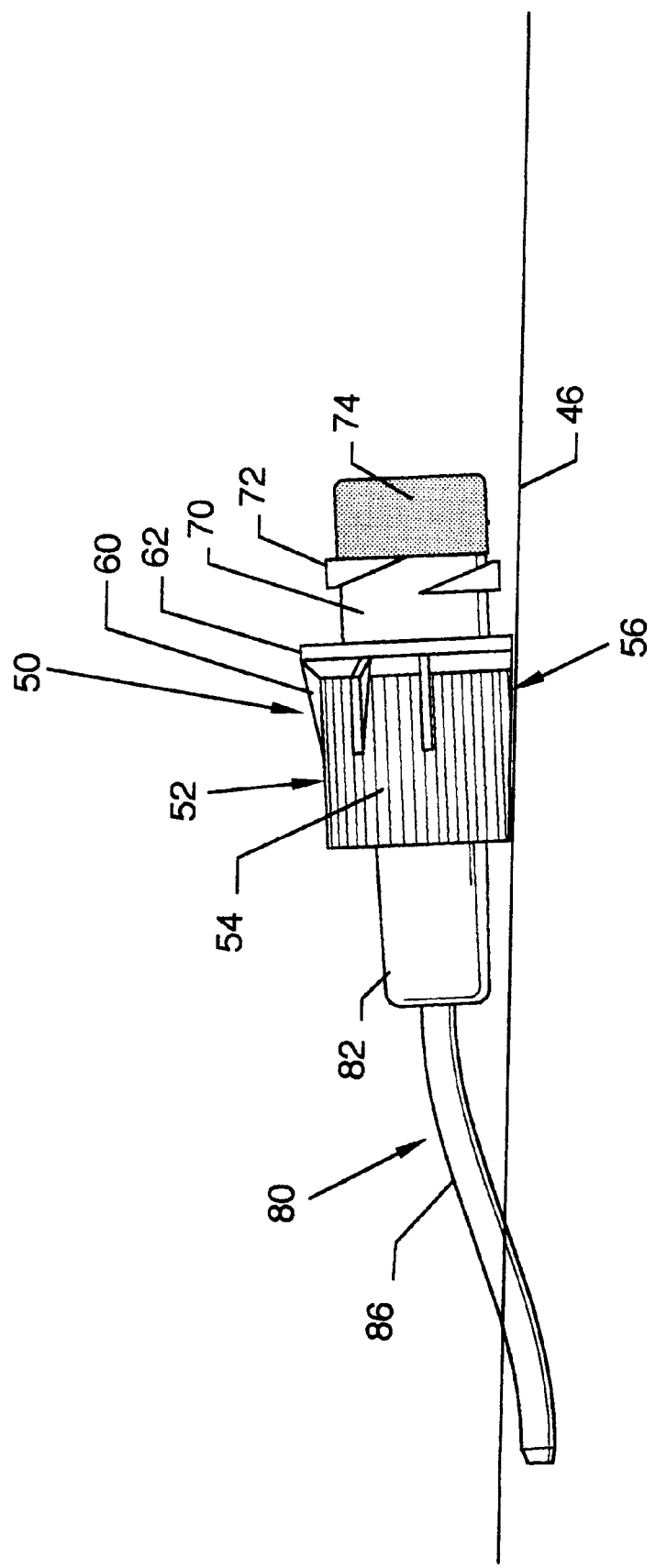

FIG. 5, an alternative embodiment, illustrates an isometric view of a flat-sided Luer lock injection site connector 50. The view presented in FIG. 5 is inverted to show the features of the flat side in full. The flat-sided Luer lock injection site connector 50 features a truncated cylindrical body 52 defined by a radiused wall 54 truncated along a chord represented by a flat planar surface 56. The wall 54 intersects the circular edge of a disk-shaped panel 58, which is also truncated. The truncated disk-shaped panel 58 extends across one end of the truncated cylindrical body 52. It should be noted that the flat planar surface 56 is angled or canted upwardly, as shown, from the proximal portion of the flat planar surface 56 to meet the level of or to rise above the level of a raised thread 72 on a cylindrical extension 70 extending distally of the truncated disk-shaped panel 58. Such an arrangement ensures that the profile of the raised thread 72 does not extend beyond the general profile of the flat-sided Luer lock injection site connector 50, thus preventing the raised thread 72 from depressed contact with the epidermis. The truncated disk-shaped panel 58, of a larger radius than the radius of the wall 54, extends across and along one end of the wall 54 to form a lip 62. Optional gussets 60 may be placed between the lip 62 and the wall 54 for adding strength to the lip 62, as illustrated in FIGS. 6–8. A plurality of threads 64a–64n are located on and extend inwardly from the inner curved surface 66 of the truncated cylindrical body 52, as shown in FIGS. 5 and 6. As with the threads 20a–20n of the flat-sided Luer lock connector 10, the threads 64a–64n of the flat-sided Luer lock injection site connector 50 are located and oriented to mate with a suitable catheter, such as intravenous catheter 34 or intravenous catheter 80 (FIG. 7). Subsequent to proper engagement of the intravenous catheter 80 with the flat-sided Luer lock injection site connector 50, the combined intravenous catheter 80 and flat-sided Luer lock injection site connector 50 are oriented to align the flat planar surface 56 parallel to the epidermis 46. Proper orientation of the threads 20a–20n of the flat-sided Luer lock connector 10 and the threads 64a–64n of the flat-sided Luer lock injection site connector 50 is desirable in that either the flat-sided Luer lock connector 10 or the flat-sided Luer lock injection site connector 50 can be suitably oriented, interchanged and attached to a catheter such as intravenous catheters 34 and 80. The threads 20a–20n of the flat-sided Luer lock connector 10 and the threads 64a–64n of the flat-sided Luer lock injection site connector 50 can be properly constructed and oriented during the manufacturing process to ensure proper orientation. A tapered tubular member 68 extends proximally and concentric to and along the centerline of the truncated cylindrical body 52 for subsequent frictional engagement to and with an intravenous catheter. Extending distally and in opposition to the tapered tubular member 68 and from the truncated disk-shaped panel 58 is the aforementioned cylindrical extension 70 having the raised thread 72 located therealong. A puncturable, self-sealing membrane 74 is fitted over and about the portion of the cylindrical extension 70 outboard of the raised thread 72 and covers the distal end of the cylindrical extension 70. The raised thread 72 can function as a stop for attached membrane-puncturing members or can serve to attach an intravenous fitting which can align over and about the membrane 74 while at the same time puncturing the membrane 74. Alternatively, an annular ring without a thread can be incorporated in lieu of the raised thread 72. Tapered tubular member 68 and cylindrical extension 70 include a common passage 78 (FIG. 6) which also extends through the truncated disk-shaped panel 58 for passage of medicinal fluids through the flat-sided Luer lock injection site connector 50. An annular space 76 (FIG. 6) is included between the inner curved surface 66 and the tapered tubular member 68 for accommodation of an intravenous catheter. Wall 54 is grooved to allow the practitioner to effectively grip the flat-sided Luer lock injection site connector 50. The truncated parts 52 and 58 impart an overall low profile to the flat-sided Luer lock injection site connector 50.

FIG. 6 illustrates a proximal end view of the flat-sided Luer lock injection site connector 50. Illustrated in particular is the common passage 78 passing through the tapered tubular member 68, the truncated disk-shaped panel 58, and the cylindrical extension 70.

FIG. 7 illustrates a side view of the flat-sided Luer lock injection site connector 50 and an intravenous catheter 80 aligned therewith prior to mutual engagement. The intravenous catheter 80 includes a tapered body 82 having a tapered interior 84, a slender and flexible cylinder 86 extending from the tapered body 82, and a passage 88 in the cylinder 86 connected to and communicating with the tapered interior 84. A flange 90 is located at one end of the tapered body 82 for engagement with the interior threads 64a–64n of the truncated cylindrical body 52.

FIG. 8 illustrates the use of the flat-sided Luer lock injection site connector 50 with the intravenous catheter 80. In use, the slender cylinder 86 of the intravenous catheter 80 is inserted through the epidermis 46, and the flat-sided Luer lock injection site connector 50 is anchored in place by taping it to the epidermis 46 with the flat planar surface 56 thereof oriented such that it lies substantially flush against the epidermis 46. Due to the flat planar surface 56 lying substantially flush against the epidermis 46, adverse effects such as trauma, irritation, stress and the like resulting from impingement of the epidermis 46 by the flat-sided Luer lock injection site connector 50 are either non-existent or exceedingly minor in nature.

Various modifications can be made to the present invention without departing from the apparent scope hereof.

Flat-Sided Luer Lock Connectors Parts List 10 flat-sided Luer lock connector
12 truncated cylindrical body
14 wall
16 flat planar surface
18 planar and truncated disk-shaped panel
20a–n threads
22 inner curved surface
24 tapered tubular member
26 cylindrical extension
28 supply tube
30 annular space
32 common passage
34 intravenous catheter
36 tapered body
38 tapered interior
40 cylinder
42 passage
44 flange
46 epidermis
50 flat-sided Luer lock injection site connector
52 truncated cylindrical body
54 wall
56 flat planar surface
58 truncated disk-shaped panel truncated
60 gusset
62 lip
64a–nthreads
66 inner curved surface
68 tapered tubular member
70 cylindrical extension
72 raised thread
74 membrane
76 annular space
78 common passage
80 intravenous catheter
82 tapered body
84 tapered interior
86 cylinder
88 passage
90 flange It is claimed is:

1. A flat-sided Luer lock connector comprising:

a. a cylindrical body truncated by a flat planar surface;

b. a truncated disk-shaped panel extending across one end of the truncated cylindrical body;

c. a cylindrical extension extending distally from the truncated disk-shaped panel for connection to a supply tube; and, d. a tapered tubular member extending proximally from an interior of the truncated cylindrical body.

* * * * *